United States Patent
Shen et al.

(10) Patent No.: US 7,556,955 B2
(45) Date of Patent: Jul. 7, 2009

(54) **NUCLEIC ACIDS ENCODING *CANDIDA KEFYR* CYTOSINE DEAMINASE**

(75) Inventors: Yuqiao Shen, Richmond, CA (US); Sylvie Laquerre, Exton, PA (US); Amy M. Delaney, Belleville, MI (US); Charles A. Omer, Ann Arbor, MI (US)

(73) Assignee: Onyx Pharmaceuticals, Inc., Emeryville, CA (US)

( * ) Notice: Subject to any disclaimer, the term of this patent is extended or adjusted under 35 U.S.C. 154(b) by 187 days.

(21) Appl. No.: 11/458,799

(22) Filed: Jul. 20, 2006

(65) Prior Publication Data

US 2007/0026491 A1   Feb. 1, 2007

Related U.S. Application Data

(62) Division of application No. 10/744,548, filed on Dec. 22, 2003, now Pat. No. 7,141,404.

(60) Provisional application No. 60/436,707, filed on Dec. 27, 2002.

(51) Int. Cl.
  *C12N 15/00* (2006.01)
  *C12P 21/00* (2006.01)
  *C07H 21/00* (2006.01)
  *C12N 9/78* (2006.01)
  *C12Q 1/34* (2006.01)
  *C12N 5/10* (2006.01)
  *C12N 1/21* (2006.01)
  *C07K 14/00* (2006.01)

(52) U.S. Cl. .............. 435/227; 435/18; 435/320.1; 435/69.1; 435/252.3; 435/325; 530/350; 536/23.1; 536/23.2; 536/23.5

(58) Field of Classification Search .......... 435/227, 435/18, 320.1, 69.1, 252.3, 325; 536/23.1, 536/23.2, 23.5; 530/350
See application file for complete search history.

(56) References Cited

FOREIGN PATENT DOCUMENTS

FR   2777570      10/1999
WO   WO99/60008 A1   11/1999

OTHER PUBLICATIONS

Branden et al., Introduction to Protein Structure, Garland Publishing Inc., New York, p. 247, 1991.*
Seffernick et al., J. Bacteriol. 183(8):2405-2410, 2001.*
Witkowski et al., Biochemistry 38:11643-11650, 1999.*
Souciet et al., GenBank accession No. AL423550, Jan. 11, 2001.*
Barylak, J., et al., Medycyna Doswiadczalna I Mikrobiologia 34:51-56 (1982).
Galagan et al., GenBank accesion No. EAA29178, 2003.
Supplementary European Search Report for EP 03814919.
Fertil B, et al., Radiat. Res. (1984) 99:73-84.
Di Vito M, et al., Antimicrob. Agents Chemother. (1986) 29(2):303-8.
Lawrence TS, Cancer Res. (1988) 48(3): 725-730.
Huber BE, et al., Proc Natl Acad Sci U S A. (1991) 88:8039-8043.
Senter PD, et al., Bioconjug. Chem. (1991) 2(6):447-51.
Freeman SM, et al., Cancer Res. (1993) 53(21):5274-5283.
Thompson JD, et al., Nucleic Acids Res. (1994)22:4673-80.
Mellon JK, et al., J Urol. (1996) 155(1):321-6. Abstract.
Erbs P, et al., Curr. Genet. (1997) 31(1) 1-6.
Hayden MS, et al., Protein Expr. Purif. (1998) 12(2):173-84.
Blom N, et al., J. Mol. Biol. (1999) 294(5): 1351-1362.
Hamstra DA, et al., Hum. Gene Ther. (1999) 10(12):1993-2003.
Tatusova TA & Madden TL, FEMS Microbiol. Lett. (1999) 174(2):247-250.
Erbs P, et al., Cancer Res. (2000) 60(14):3813-22.
Kievit E, et al., Cancer Res. (1999) 59(7):1417-1421.
Martino R, et al., Curr Drug Metab. (2000) 1(3):271-303.
Nakamura H, et al., Cancer Res. (2001) 61(14):5447-52.
Qian Q, et al., Chin Med J (Engl) (2002) 115(8):1213-1217.
Ganly I, et al., Clin Cancer Res. (2000) 6:798-806.
Goffeau A, et al., Science. (1996) 274(5287):546, 563-7.
Bussey H, et al., Nature. (1997) 387(6632 Suppl):103-5.
Ireton G, et al., Acta Cryst. (2001) D57, 1643-45.
Ireton G, et al., J. Mol. Biol. (2002) 315:687-97.
Kievet E, et al., Cancer Res. (2000) 60(23):6649-6655.
PCT Notification of Transmittal of the International Search Report or the Declaration, mailed May 11, 2006, including International Search Report re PCT/US03/41037 (5 pages).
Wong, S., Fares, M.A., Zimmermann, W., Butler, G. and Wolfe, K.H.; Evidence from comparative genomics for a complete sexual cycle in the 'asexual' pathogenic yeast *Candida glabrata*; Genome Biol. 4 (2), R10 (2003).
Wong, S., Fares, M.A., Zimmermann, W., Butler, G. and Wolfe, K.H., GenBank accession No. BZ298406 GI 24441610, 2002.

* cited by examiner

*Primary Examiner*—Delia M Ramirez
(74) *Attorney, Agent, or Firm*—Gary R. Fabian; Gregory J. Giotta

(57) ABSTRACT

A new cytosine deaminase gene and protein from *Candida kefyr* are provided. This protein has increased ability to convert the 5-fluorocytosine prodrug to its toxic form when compared against the *E. coli* enzyme.

17 Claims, 8 Drawing Sheets

Figure 1

*Candida kefyr* Cytosine deaminase cDNA SEQ.
SEQ ID NO:1 (456 nucleotides - start codon underlined)

```
1   ATGGCTGAAT GGGATCAAAA GGGTATGGAC AAAGCCTATG AAGAGGCTGC
51  CATTGGATAC AAGGAGGGAG GTGTCCCAAT CGGTGGATGT TTAATCGATA
101 ATTTGACCGG TGAGATTTTA GGCAGTGGAC ACAACATGAG ATTCCAAAAA
151 GGATCGCCTA CTTTGCACGG TGAGACTTCT ACTTTAGAAA ATGCCGGTAG
201 ACTAAAGGGG AGTGTTTACA AGCATTGTAC TATGTACACT ACTTTATCTC
251 CATGTGATAT GTGCACGGGT GCTATTCTTC TTTATGGAAT TGGCCGTGTT
301 GTCATTGGCG AAAACGTCAA CTTCAAAAGC CCTGGAGAAG AGTATCTAAC
351 CAGCAGAGGT GTGGAATTGA AGGTTGTAGA TGACAAACGC TGTATCGATA
401 TAATGAAGGA GTTCATTGAA AAGAGACCAG AAGACTGGTA CGAAGACATT
451 GGCGAA 456
```

Figure 2

*Candida kefyr* Cytosine deaminase amino acid sequence
SEQ ID NO: 2 (152 amino acids)

```
MAEWDQKGMD KAYEEAAIGY KEGGVPIGGC LIDNLTGEIL GSGHNMRFQK
GSPTLHGETS TLENAGRLKG SVYKHCTMYT TLSPCDMCTG AILLYGIGRV
VIGENVNFKS PGEEYLTSRG VELKVVDDKR CIDIMKEFIE KRPEDWYEDI
GE 152
```

Figure 3

Variant *Candida kefyr* Cytosine deaminase cDNA SEQ with mutations in bold 74C→T, 99T→C, 159T→A, 243T→C, 309C→T, 336A→G, 365A→G.
SEQ ID NO:3 (456 nucleotides - start codon underlined)

```
1    ATGGCTGAAT GGGATCAAAA GGGTATGGAC AAAGCCTATG AAGAGGCTGC
51   CATTGGATAC AAGGAGGGAG GTGTTCCAAT CGGTGGATGT TAATCGACA
101  ATTTGACCGG TGAGATTTTA GGCAGTGGAC ACAACATGAG ATTCCAAAAA
151  GGATCGCCAA CTTTGCACGG TGAGACTTCT ACTTTAGAAA ATGCCGGTAG
201  ACTAAAGGGG AGTGTTTACA AGCATTGTAC TATGTACACT ACCTTATCTC
251  CATGTGATAT GTGCACGGGT GCTATTCTTC TTTATGGAAT TGGCCGTGTT
301  GTCATTGGTG AAAACGTCAA CTTCAAAAGC CCTGGGGAAG AGTATCTAAC
351  CAGCAGAGGT GTGGAGTTGA AGGTTGTAGA TGACAAACGC TGTATCGATA
401  TAATGAAGGA GTTCATTGAA AAGAGACCAG AAGACTGGTA CGAAGACATT
451  GGCGAA
```

Figure 4

Variant *Candida kefyr* Cytosine deaminase amino acid sequence D33E underlined in bold.
SEQ ID NO: 4 (152 amino acids)

```
MAEWDQKGMD KAYEEAAIGY KEGGVPIGGC LIE NLTGEIL GSGHNMRFQK
GSPTLHGETS TLENAGRLKG SVYKHCTMYT TLSPCDMCTG AILLYGIGRV
VIGENVNFKS PGEEYLTSRG VELKVVDDKR CIDIMKEFIE KRPEDWYEDI
GE 152
```

Figure 5

```
Ckef    ------MAEWDQKSMDKAYTDAATGYKEGGVPIGCCLIDNTTGLILGGGNMPRGSPT   54
Scer    MVTGGMASK.........................IMKD.S............. .   60
Calb    -------.TED.K..LCV..DC..KKS.....S..L.SG.DDT..Q.....L.AL   53
Cyt_De          EE.E.RL..A..KRA..PYSNE..M..VLVK..D..EAL..G.NAS.D.   53

Ckef    HETSTLENAGREKGVYKHCTMYITLSPCDMCEGAIEWYGIGRVVGNVNFKSPGEE  114
Scer    .E..S..C......G.....DT.L........IM..P.C.......K..K     120
Calb    .M.A....D.W...D......L..........FK....M....LG-N.K      112
Cyt-De  .A..RNA.RK..L..FRDA..M..G........KK..A                 101

%ID
Ckef    YLTSRGVELKVVDDKRCIDIMKEFIEKRPEDWYEDIGE  152             100%
Scer    ..QT..H.VV....E...KK...Q..DE..Q..F.....  158             76%
Calb    L.IEN...VVNLN.QE..DL.AK..KEK.Q...N.....  150             57%
```

Key:
Ckef is *C. kefyr* at SEQ ID NO:2, Scer is *S. cerevisiae* at NP_015387 and SEQ ID NO:5, Calb is *C. albicans* at AAC15782 and SEQ ID NO:6, Cyt-De is the dCMP_cyt_deam consensus sequence at pfam00383.

Dot is an identical residue, Dash is a deletion, Black bars are residues identical in each of the four sequences, Gray box is the conserved domain encoding the cytidine and deoxycytidylate deaminase zinc-binding region

Figure 6

```
                                   E
Query:  AEWDQKGMDKAYEEAAIGYKEGGVPIGGCLIDNLTGEILGSGHNMRFQKGSPTLHGETST  61
        ++WDQKGMD AYEEAA+GYKEGGVPIGGCLI+N  G +LG GHNMRFQKGS TLHGE ST
Sbjct:  SKWDQKGMDIAYEEAALGYKEGGVPIGGCLINNKDGSVLGRGHNMRFQKGSATLHGEIST  67

Query:  LENAGRLKGSVYKHCTMYTTLSPCDMCTGAILLYGIGRVVIGENVNFKSPGEEYLTSRGV  121
        LEN GRL+G VYK  T+YTTLSPCDMCTGAI++YGI R V+GENVNFKS GE+YL +RG
Sbjct:  LENCGRLEGKVYKDTTLYTTLSPCDMCTGAIIMYGIPRCVVGENVNFKSKGEKYLQTRGH  127

Query:  ELKVVDDKRCIDIMKEFIEKRPEDWYEDIGE  152
        E+ VVDD+RC   IMK+FI++RP+DW+EDIGE
Sbjct:  EVVVVDDERCKKIMKQFIDERPQDWFEDIGE  158
```

Key
C. kefyr over S. cerevisiae (GenBank NP_015387) protein alignment
113/151 (74%), Positives = 132/151 (87%)
Underline: cytidine and deoxycytidylate deaminase zinc-binding region (Amino acid 3-104)
Bold: residues predicated to be significant based on change in charge and location in conserved domain. Variant D33E indicated above query sequence.

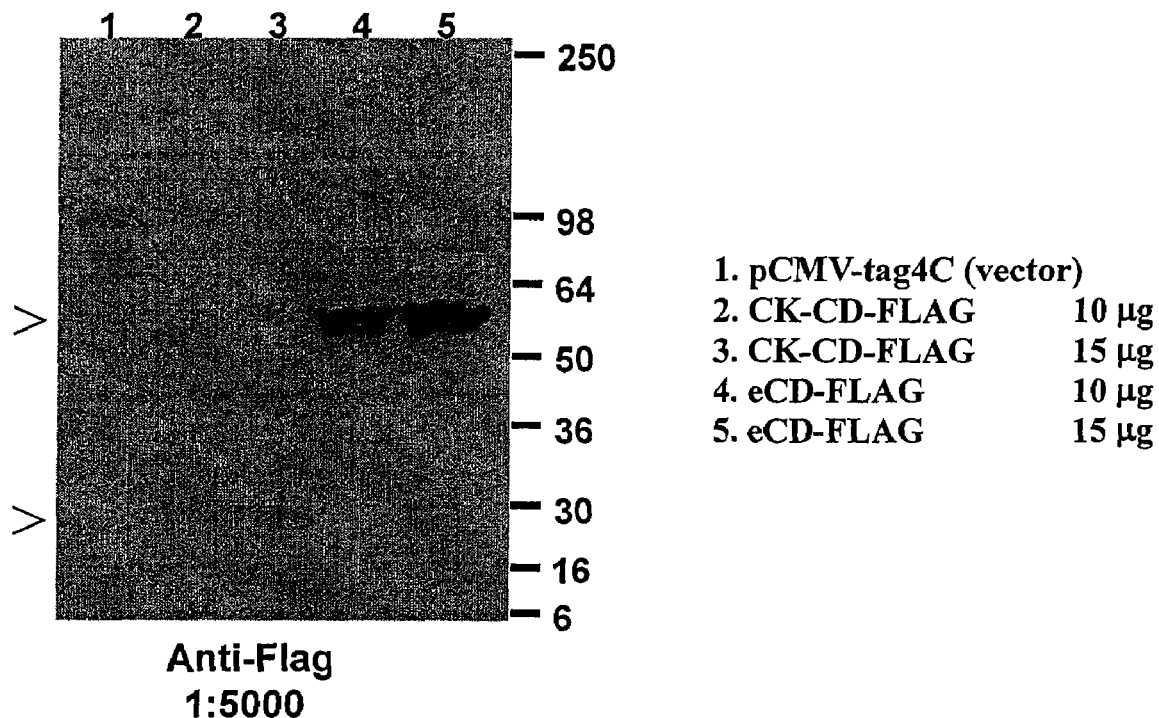

Titration of CK-CD-FLAG and E-CD-FLAG 1. pCMV-tag
2. CK-CD-FLAG          30 µl
3. E-CD-FLAG           0.5 µl
4. E-CD-FLAG           1 µl
5. E-CD-FLAG           1.5 µl
6. E-CD-FLAG           2 µl
7. E-CD-FLAG           3 µl
8. E-CD-FLAG           4 µl
9. E-CD-FLAG           5 µl
10. E-CD-FLAG          6 µl

Cytosine to Uracil Assay

5FC to 5FU Assay
at Different Temperatures

1. CK-CD-FLAG   2. CK-CD   3. E-CD-FLAG   4. E-CD   5. pCMV-tag 2-hour reaction

NUCLEIC ACIDS ENCODING *CANDIDA KEFYR* CYTOSINE DEAMINASE

PRIOR RELATED APPLICATIONS

This application is a divisional application of U.S. patent application Ser. No. 10/744,548, filed Dec. 22, 2003, now U.S. Pat. No. 7,141,404, issued Nov. 28, 2006, which claims benefit under 35 USC §119(e) to U.S. Provisional Application Ser. No. 60/436,707, filed Dec. 27 2002, now expired, entitled "*Candida kefyr* Cytosine Deaminase," both of which applications are incorporated by reference herein in their entireties.

FEDERALLY SPONSORED RESEARCH STATEMENT

Not applicable.

REFERENCE TO A SEQUENCE LISTING

A sequence listing with 24 sequence is attached hereto.

FIELD OF THE INVENTION

The invention relates to a cytosine deaminase (CD) protein and cDNA from the yeast *Candida kefyr*, variants of the same and uses thereof.

BACKGROUND OF THE INVENTION

Cytosine deaminase (CD) is an enzyme that converts cytosine to uracil. The bacterial and fungal versions of this enzyme can also convert 5-fluorocytosine (5FC) to 5-fluorouracil (5FU). However, the human and mouse enzyme does not recognize 5FC as a substrate. Bacterial and fungal CD converts 5FC to 5FU, which is then converted to 5-fluoro-deoxyuridine monophosphate (5FdUMP) in all species. 5FdUMP is an irreversible inhibitor of thymidylate synthase, and the accumulation of 5FdUMP leads to cell death by inhibiting DNA synthesis via deoxythymidine triphosphate (dTTP) deprivation.

Because the human CD gene does not convert 5FC to 5FU, the pro-drug 5FC is only toxic in those human cells that are engineered to express a bacterial or fungal CD gene. This has been used to advantage in treating tumors, and is an example of a "suicide gene" system. The tumors are transformed with a bacterial or fungal CD gene, usually by direct injection, implantation or systemic administration of a vector containing the CD gene. The patient is then treated with 5FC and the toxic effects of 5FU lead to death of the transformed cells that continue to divide.

The suicide gene system has been studied extensively as an approach to treat malignant tumors. One of the advantages of the system is that incorporation of the suicide gene into every tumor cell is not necessary for effective therapy; complete tumor responses have been reported in animals when less than 20% of the cells expressed the suicide gene. This phenomenon is known as the "bystander effect," and is based on the continued toxicity of the drug to neighboring cells when a particular cell dies and releases its drug load (6).

The suicide gene system requires accurate targeting because gene expression in a normal cell followed by exposure to the pro-drug will kill the cell when it attempts to divide. This problem has been addressed by placing the suicide gene under control of a tissue-specific (or preferentially a tumor-specific) promoter so that the gene will be expressed only in a select population of targeted cells. The alpha-fetoprotein promoter, which is preferentially activated in hepatoma cells, is an example of such an approach (8). Because many promoter sequences are not completely tumor specific, the suicide gene may be also be expressed in some amount of healthy tissue. This is not fatal to efficacy, however, because like most chemotherapy, the premise of the treatment is that actively dividing cells are preferentially targeted by the drug.

Although suicide genes are a promising approach for the specific targeting of tumors, there is room for improvement in most aspects of the system. In particular, an enzyme with increased activity would allow the use of lower doses of 5FC, and avoid the reported immunosuppressive effects of high 5FC doses. The present invention provides one such improvement.

SUMMARY OF THE INVENTION

The term "fusion" is used to refer to chemically linked polypeptides (or nucleic acid encoding such polypeptide), to another peptide (or nucleic acid encoding same) with a known property which can be utilized to impart the known property on the entire fusion protein. The use of fusions is common in the art to facilitate protein purification and for visualizing the protein of interest. An example of a protein fusion is the expression of proteins from vector where the protein is operably linked to an intein (a self cleaving protein) which is operably linked to a binding domain. By affixing the substrate of the binding domain to a solid surface, the protein of interest can be bound to the surface, rinsed, and released under conditions which induce intein cleavage. Other examples of fusions include the use of antigenic tags (such as HIS or FLAG) that can be used to isolate or visualize the tagged protein.

The term "humanized," as used herein, refers to protein coding sequences in which the codons have been converted to codons utilized more frequently in a human gene, while still retaining the original amino acid sequence. Similarly, "*E. coli* bias" refers to a gene optimized for expression in *E. coli*.

The term "isolated," as used herein, refers to a nucleic acid or polypeptide removed from its native environment. An example of an isolated protein is a protein bound by a polyclonal antibody, rinsed to remove cellular debris, and utilized without further processing. Salt-cut protein preparations, size fractionated preparation, affinity-absorbed preparations, recombinant genes, recombinant protein, cell extracts from host cells that expressed the recombinant nucleic acid, media into which the recombinant protein has been secreted, and the like are also included. The term "isolated" is used because, for example, a protein bound to a solid support via another protein is at most 50% pure, yet isolated proteins are comrnonly and reliably used in the art.

"Purified," as used herein refers to nucleic acids or polypeptides separated from their natural environment so that they are at least 95% of total nucleic acid or polypeptide in a given sample. Protein purity is assessed herein by SDS-PAGE and silver staining. Nucleic acid purity is assessed by agarose gel and EtBr staining.

The term "substantially purified," as used herein, refers to nucleic acid or protein sequences that are removed from their natural environment and are at least 75% pure. Preferably, at least 80, 85, or 90% purity is attained.

The phrases "nucleic acid" or "nucleic acid sequence," as used herein, refers to polynucleotides, which may be gDNA, cDNA or RNA and which may be single-stranded or double-stranded. The term also includes peptide nucleic acid (PNA), or to any chemically DNA-like or RNA-like material. "cDNA" refers to copy DNA made from mRNA that is naturally occurring in a cell. "gDNA" refers to genomic DNA. Combinations of the same are also possible (i.e., a recombinant nucleic acid that is part gDNA and part cDNA).

"Fragments" refers to those polypeptides (or nucleic acid sequences encoding such polypeptides) retaining antigenicity, a structural domain, or an enzymatic activity of the full-length protein. The "enzymatic activity" of the CD protein is herein defined to be the conversion of 5FC to 5FU. "Structural domains" including the conserved cytosine deaminase domain (residues 3-104) are as indicated in FIG. 5.

The term "oligonucleotide," as used herein, refers to a nucleic acid sequence of at least about 15 nucleotides to 100 nucleotides, and all integers between. Preferably, oligonucleotides are about 18 to 30 nucleotides, and most preferably about 20 to 25 nucleotides. Generally, an oligonucleotide must be greater than 22 to 25 nucleotides long for specificity, although shorter oligonucleotides will suffice in certain applications.

The terms "operably associated" or "operably linked," as used herein, refer to functionally coupled nucleic acid sequences.

A "variant" of CD polypeptides, as used herein, refers to an amino acid sequence that is altered by one or more amino acid residues. Such variations may be naturally occurring or synthetically prepared. Common variants include "conservative" changes, truncations, and domain removal or swapping with similar proteins. Guidance in determining which amino acid residues may be substituted, inserted, or deleted without abolishing biological ox immunological activity may be found using computer programs well known in the art, for example, LASERGENE™ software, and comparison against the many known CD genes.

The term "naturally occurring variant," includes those protein or nucleic acid alleles that are naturally found in the population in question. The naturally occurring allelic variants may be point, splice, or other types of naturally occurring variations.

"High Stringency" refers to wash conditions of 0.2×SSC, 0.1% SDS at 65° C. "Medium stringency" refers to wash conditions of 0.2×SSC 0.1 % SDS at 55° C.

In calculating "% identity" the unaligned terminal portions of the query sequence are not included in the calculation. The identity is calculated over the entire length of the reference sequence, thus short local alignments with a query sequence are not relevant (e.g., % identity=number of aligned residues in the query sequence/length of reference sequence). Alignments are performed using BLAST homology alignment as described by Tatusova T A & Madden T L (1999) FEMS Microbiol. Lett. 174:247-250. The default parameters were used, except the filters are turned OFF. As of Jan. 1, 2001 the default parameters were as follows: BLASTN or BLASTP as appropriate; Matrix=none for BLASTN, BLOSUM62 for BLASTP; G Cost to open gap default=5 for nucleotides, 11 for proteins; E Cost to extend gap [Integer] default=2 for nucleotides, 1 for proteins; q Penalty for nucleotide mismatch [Integer] default=−3; r reward for nucleotide match [Integer] default=1; e expect value [Real] default=10; W wordsize [Integer] default=11 for nucleotides, 3 for proteins; y Dropoff (X) for blast extensions in bits (default if zero) default=20 for blastn, 7 for other programs; X dropoff value for gapped alignment (in bits) 30 for blastn, 15 for other programs; Z final X dropoff value for gapped alignment (in bits) 50 for blastn, 25 for other programs. This program is available online at www.ncbi.nlm.nih.gov/BLAST/.

Candida kefyr (a.k.a. Candida pseudotropicalis, Kluyveromyces marxianus, Kluyveromyces fragilis) CD is an improvement over the several prior art cytosine deaminase proteins. C. kefyr CD has significantly lower expression levels than E. coli CD (to date), but its activity is much higher in converting 5FC to 5FU. Further, 5FC is a better substrate for C. kefyr CD than is the natural substrate, cytosine. Table 1 provides a listing of sequences taught herein.

TABLE 1

| SEQ ID NO AND DESCRIPTION | | | |
|---|---|---|---|
| SEQ ID NO: | TYPE | Length | Name and Description |
| 1 | cDNA | 456 nt | Wild type Candida kefyr CD cDNA |
| 2 | Peptide | 152 aa | Wild type Candida kefyr CD protein |
| 3 | cDNA | 456 nt | Variant Candida kefyr CD cDNA with 74C→T, 99T→C, 159T→A, 243T→C, 309C→T, 336A→G, 365A→G |
| 4 | Peptide | 152 aa | Variant Candida kefyr CD protein D33E |
| 5 | Peptide | 158 aa | Wild type Saccharomyces cerevisiae CD protein |
| 6 | Peptide | 150 aa | Wild type Candida albicans CD protein |
| 7 | cDNA | 459 nt | E. coli biased Candida kefyr CD cDNA (incl. stop codon) |
| 8 | cDNA | 459 nt | Humanized Candida kefyr CD cDNA (incl. stop codon) |
| 9 | cDNA | 459 nt | Humanized Candida kefyr CD cDNA with immunogenic CpG's removed (incl. stop codon) |
| 10 | cDNA | 1104 nt | Candida kefyr CD-uracil phosphoribosyltransferase (FUR1) fusion protein cDNA. |
| 11 | Oligo | 18 | Probe 1 |
| 12 | Oligo | 18 | Probe 2 |
| 13 | Oligo | 18 | Probe 3 |
| 14 | Oligo | 15 | Probe 4 |
| 15 | Oligo | 15 | Probe 5 |
| 16 | Oligo | 30 | CK 5' Long |
| 17 | Oligo | 30 | CK 3' Long |
| 18 | Oligo | 33 | CK 5' Nest |
| 19 | Oligo | 30 | CK 3' Nest |
| 20 | Oligo | 39 | CK 5' BamH1 |
| 21 | Oligo | 32 | CK 3' Xho1 (no stop) |
| 22 | Oligo | 33 | CK 3' Pst1 (stop) |
| 23 | Peptide | 16 | C. kefyr CD Epitope 1 |
| 24 | Peptide | 18 | C. kefyr CD Epitope 2 |

Other protein variants are described in Table 2 with reference to SEQ ID NO: 2.

TABLE 2

| CD VARIANTS | | |
|---|---|---|
| SEQ ID NO: 2 Variant | % ID | Activity |
| D33E-3'FLAG | 151/152 (99%) | Mutant tested and has less activity than the protein of SEQ ID NO: 2 |
| D33E | 151/152 (99%) | Mutant not yet made, but may have decreased activity |

TABLE 2-continued

CD VARIANTS

| SEQ ID NO: 2 Variant | % ID | Activity |
| --- | --- | --- |
| I92L/L93I/I97L | 149/152 (98%) | Expected to have 800 fold less than wild-type because this mutant is shown to be less active in other yeast species. See WO199960008. |
| T80S/T81S/T89S/Y95S | 148/152 (97%) | Expected to have 800 fold less than wild-type, see above. |
| S42K/R47K | 150/152 (99%) | Expected to have 100 fold less than wild-type, see above. |
| K129R/K136R | 150/152 (99%) | Expected to have 800 fold less than wild-type, see above. |
| Δ1 | 151/152 (99%) | Met-free variant, expected to have wild type activity. |
| Δ1-2 | 150/152 (99%) | Deleting first two amino acids which are missing in the consensus protein, expected to have activity. |
| Δ1-8 | 144/152 (95%) | Alternate start codon, expected to have activity. |
| Δ1-9 | 143/152 (94%) | Met-free variant using alternate start codon, encodes the cytidine and deoxycytidylate deaminase zinc-binding region, expected to have some activity. |
| Single E to D mutations, at positions 3, 38, 114, 138 | 151/152 (99%) | Not expected to change activity since change conservative and residue not conserved in yeast. |
| Single D to E mutation at position 33 | 151/152 (99%) | Not expected to change activity since change conservative and residue not conserved in yeast. |
| Single K to R mutation, esp. at positions 11, 69, 124, 129, and 141 | 151/152 (99%) | Not expected to change activity since change conservative and residue not conserved in yeast. |

The invention is generally directed to protein and gene or cDNA sequence of *C. kefyr* cytosine deaminase of amino acid sequence of SEQ ID NO: 2 or SEQ ID NO: 4. Variations of the cDNA encoding the protein are provided, including an *E. coli* biased CD cDNA (SEQ ID NO: 7), a humanized CD cDNA (SEQ ID NO: 8), and a humanized and CpG-free CD cDNA (SEQ ID NO: 9). Fusions are also provided, in particular the CD-uracil phosphoribosyltransferase fusion (SEQ ID NO: 10) and a CD-FLAG fusion (see table 2).

The nucleic acid sequences can be used in traditional suicide gene therapy methodologies. Suicide gene therapies are in phase I, II and III clinical trials, and are well established treatment supplements or alternatives. The *C. kefyr* gene provides an advantage over current suicide gene sequences because lower amounts of 5FC are needed for therapy, due to the protein's improved ability to convert 5FC to 5FU. The gene also has uses in preparing large amounts of protein for biochemical characterization, preparation of antibodies, and the like.

A large number of variant protein sequences are provided, based on both the known homologies with prior art sequences and on the predicted characteristics of the protein, as shown in tables 1-3 and FIGS. 5 and 6. The range of mutants provided all are within 94% amino acid identity to the wild type sequence as disclosed. The closest prior art sequence has only 74% amino acid identity to the *C. kefyr* cytosine deaminase protein.

Antigenic fragments of *C. kefyr* cytosine deaminase are also provided, which have already been used to successfully generate antibodies of the invention. The antigenic fragments can be selected to be unique or conserved, as shown in table 5. Similarly, fragments of the nucleotide sequence of SEQ ID NO: 1 or 3 can be used as oligonucleotide probes or as primers in a variety of methods. Larger fragments can also be used as probes.

BRIEF DESCRIPTION OF THE DRAWINGS

FIG. 1. *Candida kefyr* Cytosine deaminase cDNA sequence (SEQ ID NO: 1). The cDNA was cloned by PCR amplification using primers from those portions of sequence that were conserved among the prior art fungal sequences.

FIG. 2. *Candida kefyr* Cytosine deaminase amino acid sequence (SEQ ID NO: 2). The amino acid sequence was derived from the nucleotide sequence of the cDNA.

FIG. 3. Variant *Candida kefyr* Cytosine deaminase cDNA sequence with 74C→T, 99T→C, 159T→A, 243T→C, 309C→T, 336A→G, 365A→G (SEQ ID NO: 3). The variant CD protein was obtained from a different clone amplified using the previously described system.

FIG. 4. Variant *Candida kefyr* Cytosine deaminase amino acid sequence D33E (SEQ ID NO: 4). The amino acid sequence was derived from the nucleotide sequence of the cDNA in FIG. 3.

FIG. 5. CD Multiple Sequence Alignment with *Candida kefyr* (SEQ ID NO: 2), *S. cerevisiae* (SEQ ID NO: 5), *C. albicans* (SEQ ID NO: 6), and the CD consensus sequence. The *S. cerevisiae* sequence was obtained from GenBank accession number $NP_{13}$ 015387. The *C. albicans* sequence was obtained from GenBank accession number AAC15782. The consensus sequence was obtained from the Pfam database of protein domains and HMMs (pfam.wustl.edu/index.html) accession number PF00383. The sequences in FASTA format were aligned according to Higgins (7), using the default parameters (www.ebi.ac.uk/clustalw). Default settings as of Jun. 20, 2002 were: CPU mode=clustalw_mp; alignment=full; output format=aln w/numbers; output order=aligned; color alignment=no; KTUP=def; window length=def; score=percent; topdiag=def; pairgap=def; phylogenetic tree=none (off, off); matrix=def; gap open=def; end gaps=def; gap extension=def; gap distances=def; tree type=cladogram; tree gap distance=hide.

FIG. 6. Pairwise alignment with *Candida kefyr* (SEQ ID NO: 2) and *S. cerevisiae* (SEQ ID NO: 5) sequences. Sequences were aligned at www.ncbi.nlm.nih.gov/BLAST/.

FIG. 7. Western Blot Using Anti-FLAG. An anti-FLAG antibody is used to confirm expression of the CD constructs, including CK-CD-FLAG and E-CD-FLAG. The bacterial protein is much more strongly expressed than the yeast protein.

DESCRIPTION OF EMBODIMENTS OF THE INVENTION

Figure 8:
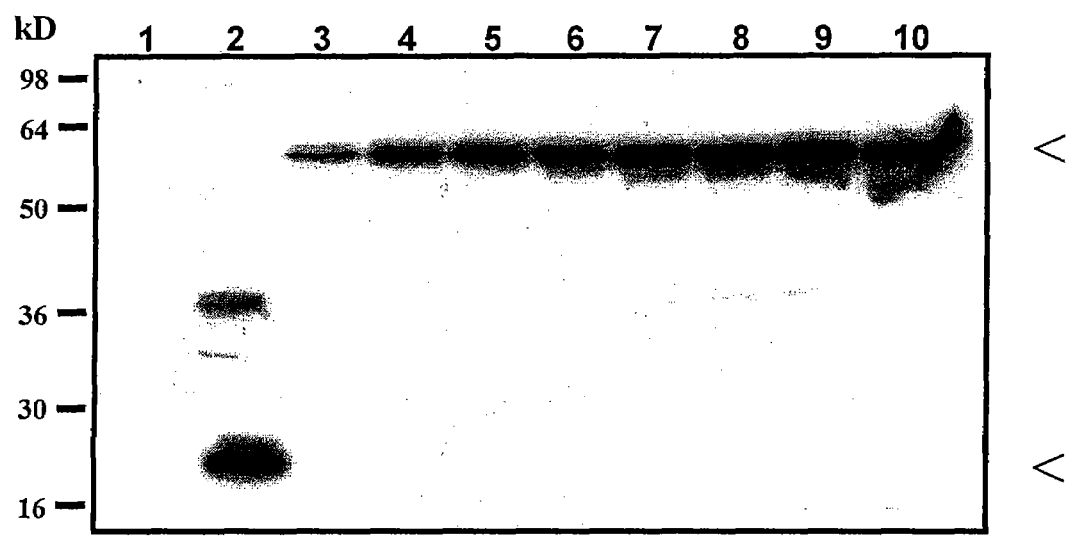
FIG. 8. Titration of CK-CD-FLAG and E-CD-FLAG. 30 μl of CK-CD-FLAG lysate is about equal to 3 μl of E-CD-FLAG lysate when tested by Western blot with anti-FLAG antibody. This suggests that the CK-CD-FLAG protein is about ten-fold less well expressed than the E-CD-FLAG. Yet, control experiments (with a co-transfected GFP containing vector, not shown) show roughly equivalent transfection efficiencies.

The present invention is directed to the *Candida kefyr* cytosine deaminase (CK-CD) protein and cDNA sequence. Also included are i) *E. coli* biased and humanized DNA sequences encoding CD, ii) antigenic polypeptide fragments and antibodies to same, iii) variants predicted to retain functional activity based on comparison with the large number of proteins in this family and inactive mutants, iv) naturally occurring variants, v) fusion proteins, such as FLAG, GFP, luciferase, uracil phosphoribosyltransferase, and monoclonal antibody fusions.

| Primer | Sequence |
|---|---|
| Probe 1 = SEQ ID NO: 11 | ATG TGT ACT GGT GCT ATT |
| Probe 2 = SEQ ID NO: 12 | GGT GAA AAC GTT AAC TTC |
| Probe 3 = SEQ ID NO: 13 | GGT GAA AAC GTC AAC TTC |
| Probe 4 = SEQ ID NO: 14 | GAA GAT ATT GGT GAA |
| Probe 5 = SEQ ID NO: 15 | GAA GAC ATT GGT GAA |

Polymerase chain reaction was performed with the described primers and 0.1 μg genomic DNA under the following conditions:

```
1 μl (0.1 μg) DNA
1 μl dNTP mix (10 μM)
5 μl 10× Pfu polymerase buffer
1 μl Probe 1 (5' primer) (10 μM)
1 μl Probe 2, 3, 4, or 5 (3' primer) (10 μM)
1 μl Pfu Turbo polymerase (4 units) (STRATAGENE ™)
40 μl ddH2O
```

Reaction conditions were as follows: 94° C. for 3 minutes (1 cycle), followed by 25 cycles of 94° C. 45 seconds, 40° C. for 45 seconds, 72° C. for 30 seconds. Ten μl of the reactions were run on a 3% agarose gel. Based on the sequence alignment of the known CD genes, expected fragment sizes were expected to be between 66 and 200 base pairs, depending on primer set used in reaction, and the CK PCR produced the expected fragments. These fragments were excised from the agarose gel and subdloned into pCRScript cloning vector (STRATAGENE™, La Jolla, Calif.). Plasmid DNA was purified and analyzed by restriction digest for clones containing correct insert size. The plasmid DNA was sequenced by ResGen Laboratories (INVITROGEN™, Carlsbad, Calif.).

Based on the sequence of the clones described above, primers were designed and synthesized for use in a Genome Walker kit (CLONTECH™, Palo Alto, Calif.) to isolate the full length CD gene of *C. kefyr*. The oligonucleotides used with the kit were as follows:

| Primer | Sequence |
|---|---|
| CK 5' Long = SEQ ID NO: 16 | GGCCGTGTTGTCATTGGTGAAAACGTCAAC |
| CK 3' Long = SEQ ID NO: 17 | GGTCTCTTTTCAATGAACTCCTTCATTATA |
| CK 5' Nest = SEQ ID NO: 18 | GTTGTCATTGGTGAAAACGTCAACTTCAAAAGC |
| CK 3' Nest = SEQ ID NO: 19 | AATGAACTCCTTCATTATATCGATACAGCG |

EXAMPLE 1

Cloning and Sequence Characterization of CD

Genomic DNA for *Candida kefyr* was purchased from ATCC. Amino acid sequence alignment of known fungal cytosine deaminase genes FCA1 (*C. albicans*) and FCY1 (*S. cerevisiae*) were used to design degenerative primers for regions of the genes that were homologous. The oligonucleotides were as follows:

"Libraries" were created and PCR performed as described in the Genome Walker kit protocol. The PCR products were subcloned into pcDNA2.1 (INVITROGEN™), plasmid DNA purified and clones sent for sequencing to ResGen Laboratories. Sequences for the 5' and 3' ends of *C. kefyr* gene were determined and oligonucleotides containing restriction enzyme sites (italicized) and a mammalian Kozak sequence (bold) were designed and synthesized as follows:

| Primer | Sequence |
| --- | --- |
| CK 5'BamH1 = SEQ ID NO: 20 | CTTGGGATCCGCCACCATGGCTGAATGGGATCAAAAGGG |
| CK 3'Xho1(no stop) = SEQ ID NO: 21 | CTTGCTCGAGTTCGCCAATGTCTTCGTACCAG |
| CK 3'Pst1(Stop) = SEQ ID NO: 22 | CTTGCTGCAGCTATTCGCCAATGTCTTCGTACC |

The full length CD gene was isolated via PCR from *C. kefyr* genomic DNA under the following conditions:

```
2 µl (0.2 µg) genomic DNA
1 µl dNTP mix (10 µM)
5 µl 10X Pfu rxn buffer
1 µl 5' primer (10 µM)
1 µl 3' primer (10 µM)
1 µl Pfu Turbo DNA polymerase (4 units)
39 µl ddH2O
```

25 cycles at 94° C. for 30 seconds, 65° C. for 30 seconds and 72° C for 1 minute were run in a thermocycler. PCR products were analyzed by agarose gel with ethidium bromide staining. The fragments were digested with the appropriate restriction enzymes and subcloned by standard methods into pCMV4A vector (STRATAGENE™). The sequence of cytosine deaminase gene was confirmed by ResGen Laboratories.

The clone containing the gene was deposited at ATCC PTA-4867. The cloned insert was sequenced and is presented in FIG. 1, the translation product in FIG. 2. A naturally occurring allelic variant is shown in FIGS. 3 and 4. The protein of SEQ ID NO: 2 is 152 amino acids and is characterized as follows:

EXAMPLE 2

Expression of CD

Human embryonic kidney cells (HEK 293 cells) were transiently transfected with one of these constructs: CK-CD-FLAG, CK-CD, E-CD-FLAG, E-CD or vector alone (pCMV-tag4C). Control experiments were performed to confirm that each construct was transfected with comparable efficiency. Cells co-transfected with a construct and a GFP containing plasmid indicated approximately equivalent levels of transfection.

The experimental details are as follows: 293 cells in 10 cm dishes were transfected with 10 or 15 µg of CD constructs using FuGene 6 (ROCHE™) at a DNA/FuGene ratio of 1:3. No carrier DNA was used. Cell lysates were collected in 1 ml of lysis buffer (20 mM Tris-Cl, pH8, 150 mM NaCl, 1% Triton X-100) after 48 hours by three freeze/thaw cycles using dry ice for 10 minutes and room temperature for 10 minutes.

30 µl of cell lysate was separated by 12% SDS-PAGE, transferred to membrane and then Western blotted with anti-flag monoclonal antibody at a dilution of 1:5000 (SIGMA™). The membranes were incubated with HRP conjugated goat-anti-mouse secondary antibody (1:10000, AMERSHAM™) and the signal visualized with an ECL system (AMERSHAM™). The data in FIG. 7 shows that *E. coli* CD-FLAG is

TABLE 3

GENERAL CHARACTERISTICS
Number of amino acids: 152
Molecular weight: 16819.1
Theoretical pI: 4.95
Amino acid composition:

| Ala 6 | Arg 9 | Asn 5 | Asp 9 | Cys 5 | Gln 2 | Glu 16 | Gly 20 | His 3 | Ile 11 |
| --- | --- | --- | --- | --- | --- | --- | --- | --- | --- |
| 3.9% | 3.9% | 3.3% | 5.9% | 3.3% | 1.3% | 10.5% | 13.2% | 2.0% | 7.2% |
| Leu 11 | Lys 11 | Met 6 | Phe 3 | Pro 5 | Ser 7 | Thr 9 | Trp 2 | Tyr 7 | Val 8 |
| 7.2% | 7.2% | 3.9% | 2.0% | 3.3% | 4.6% | 5.9% | 1.3% | 4.6% | 5.3% |
| Asx 0 | Glx 0 | Xaa 0 | | | | | | | |
| — | — | — | | | | | | | |

Total number of negatively charged residues (Asp + Glu): 25
Total number of positively charged residues (Arg + Lys): 17
Formula: C735H1156N196O233S11 Total number of atoms: 2331
Estimated half-life: The N-terminal of the sequence considered is M (Met). The estimated half-life is: 30 hours (mammalian reticulocytes, in vitro). >20 hours (yeast, in vivo). >10 hours (*Escherichia coli*, in vivo). Instability index: The instability index (II) is computed to be 35.20. This classifies the protein as stable. Aliphatic index: 75.66
Grand average of hydropathicity (GRAVY): −0.410
There are no predicted myristolation sites or n-terminal signal sequences.
There is a potential cleavage site at amino acid 118.

expressed much more efficiently than *Candida kefyr* CD-FLAG, although they were constructed in the same vector. Similar results were obtained (not shown) when the cells were transfected with 2 μg of each DNA construct. Experiments are planned to test a humanized *C. kefyr* gene and it is expected that the humanized gene will improve the expression levels.

Because the bacterial protein was more strongly expressed than the yeast protein, an attempt was made to compare the levels for the amount of expression of the two clones. In a second Western blot, 30 μl of CK-CD-FLAG was compared against increasing amounts of E-CD-FLAG. As seen in FIG. 8, 30 μl of CK-CD-FLAG (~18KD band) is roughly equivalent to 4 μl of E-CD-FLAG (~60 KD band), indicating about 7.5-fold better expression. In the following experiments, this ratio of cell lysates is used. The presence of a fainter band at about 38 KD may indicate that some portion of the CK-CD protein dimerizes.

EXAMPLE 3

Enzymatic Assay

For conversion assays, 1 μl of 100 μCi/ml either $^{14}$C-cytosine or $^{14}$C-5FC (MORAVEK BIOCHEMICALS™) was added to 45 μl of yeast CD or 6 μl of bacterial CD cell lysates and incubated at the indicated temperatures for 2 or 16 hours. The reaction mixtures were loaded onto a TLC plate (LK5DF SILICA GEL, Cat. No. 4856-821, WHATMAN™) and resolved with 1-butanol:H$_2$O (85:15) for 3 hours. The plate was then dried and visualized by autoradiography. However, CD activity can also be assayed by 19F nuclear magnetic resonance (NMR) as described by De Vito (2) and Martino (17).

Figure 9:
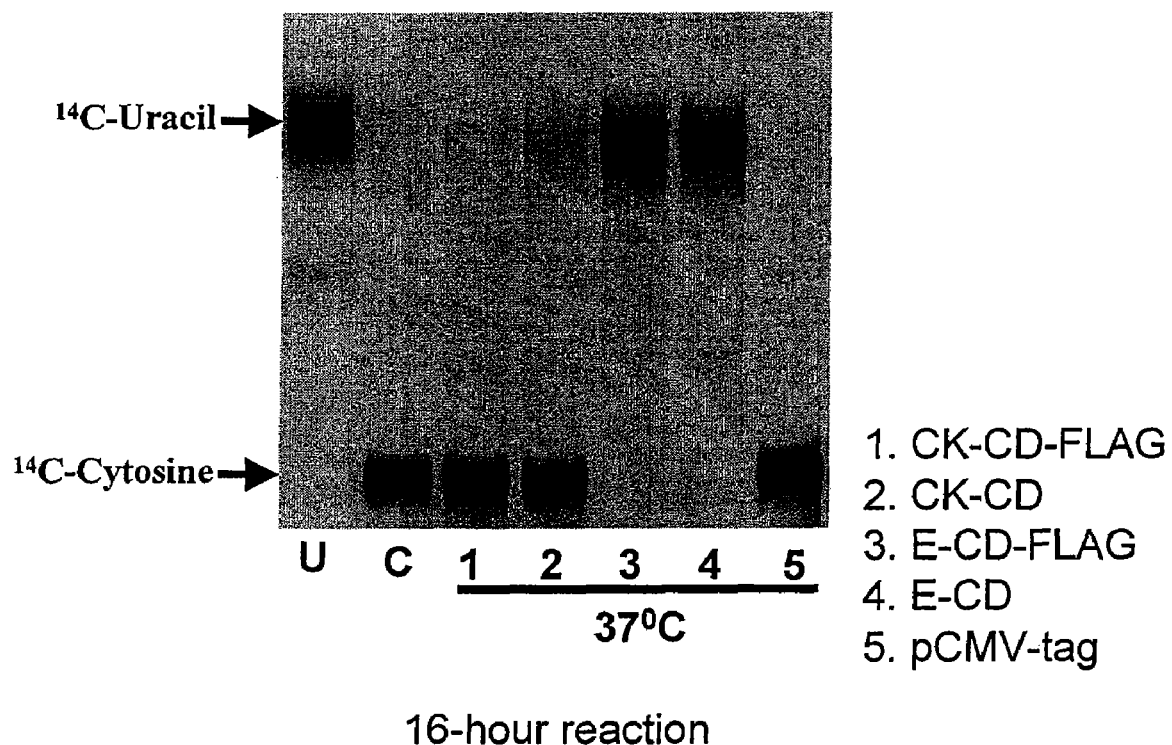
FIG. 9. Cytosine to Uracil Assay. Equal amounts of cell lysate are assayed for cytosine to uracil conversion at 37° C. in a 16 hour assay. Activities of CK-CD-FLAG, CK-CD, E-CD-FLAG, and E-CD are shown, and it is apparent that CK-CD without the FLAG tag is much more active than the protein with the FLAG tag. This may represent increased expression or activity or some combination thereof.

Cell lysates were assayed for cytosine to uracil conversion at 37° C. in a 16 hour assay. The activities of CK-CD-FLAG (with the D33E variation), CK-CD, E-CD-FLAG, and E-CD are shown in FIG. 9. It is apparent that CK-CD without the FLAG tag is much more active than the protein with the tag (compare lanes 1 and 2). This may represent increased expression or increased activity or some combination thereof. This may also reflect the D33E mutation in the CD-FLAG variant. Because the CK-CD protein is very small, it is anticipated that the FLAG may inhibit its activity, although the prior figure also indicates that expression is also inhibited.

The *C. kefyr* CD protein was found to be far less active against cytosine than was the *E. coli* CD protein (compare lanes 2 and 4). This probably reflects the fact that the assay conditions employed were optimized for the *E. coli* protein. Further, although bacterial activity seems to increase with increased reaction time (not shown), that of the yeast protein does not. This is confirmed in an independent assay (not shown), and may indicate that under these conditions the yeast enzyme is slightly less stable than the bacterial enzyme.

The *S. cerevisiae* protein is also known to be thermally instable (measured $T_{1/2}$=1 hr, (16)). However, structural analysis indicates that both yeast proteins should be more stable in mammalian cells (calculated $T_{1/2}$>30 hours, see Tables 3-4). Thus, we expect that the stability can be improved by optimizing the reaction conditions and this work is underway.

Figure 10:
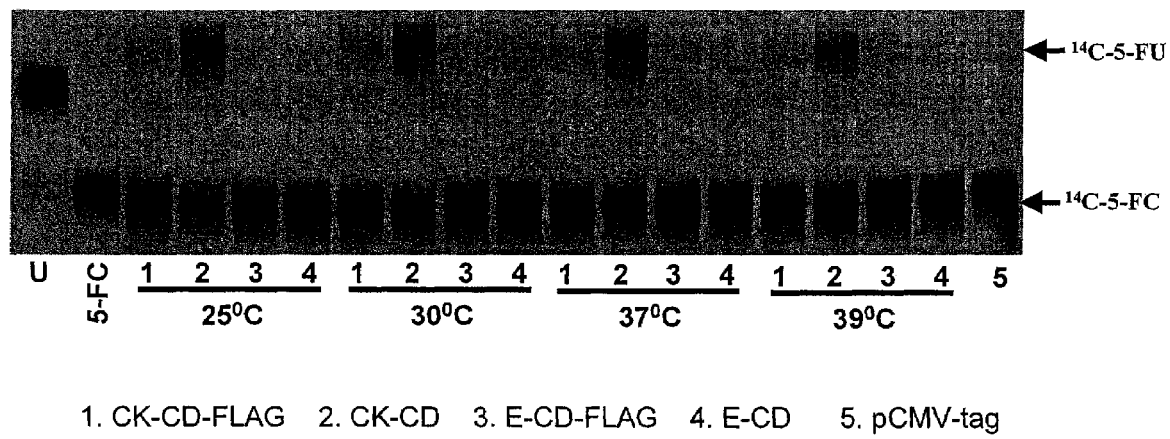
FIG. 10. 5FC to 5FU Assay at Different Temperatures. Equal amounts of cell lysate are assayed for cytosine to uracil conversion at 37° C. in a 2 hour assay at the indicated temperatures. CK-CD is much more active than CK-CD-FLAG, and this may reflect better expression, activity or both. Both tagged and untagged yeast CD are more active against 5FC than the bacterial protein.

In the next experiment, we tested the activity of each enzyme against 5FC. The experiment was performed as described above, but using 5FC in place of cytosine. Further, this experiment was combined with a temperature optimization study and was performed at 4 different temperatures. As shown in FIG. 10, the yeast protein had a lower temperature optima than the bacterial protein, probably reflecting typical ambient growth conditions for each organism. However, the *C. kefyr* protein was sufficiently active at 37° C. for it to be useful in human therapies. Further, a variant with increased stability can be isolated by screening yeast grown at 37° C., as described in the Examples below.

Although the CK-CD protein was less active against cytosine, it is unexpectedly more active against 5FC than is the *E. coli* CD at 2 hours. This is shown in FIG. 10 where the yeast protein shows much better conversion of 5FC to 5FU (compare lanes 1 and 3 or 2 and 4). At 16 hours of reaction, the bacterial protein produces as much or more 5FU than the yeast protein (not shown), but as discussed above, this probably reflects the better stability of the bacterial protein under the reaction conditions employed.

The experiment demonstrates that yeast protein is more active than the bacterial protein against the pro-drug 5FC. Thus, the *Candida kefyr* CD gene and protein will provide an advantage in suicide gene therapy, because decreased dosage of 5FC can be employed while still achieving cytotoxicity. Experiments are underway to confirm that the specific activity of the yeast protein against 5FC is significantly greater than that of the bacterial protein.

Using the above assay, the enzyme was further characterized and compared against the existing cytosine deaminase proteins. The results are as follows:

TABLE 4

| | | | | | | | |
|---|---|---|---|---|---|---|---|
| | | | | YEAST CD COMPARISON | | | |
| CD Species | AMINO ACID | % identity | T½ HR | Preferred Buffer | Vmax μM/min/μg enzyme | Km mM | Activity % 5FU/5FC by 0.2 μg CD in 2 h |
| *Candida kefyr* | 152 | 100% | >30 | n/a | n/a | n/a | ~50% by 45 ul cell extract |
| *S. cerevisiae* FCY1 | 158 | 74% 131/151 | >30 ($^{16}$1) | $^{16}$100 mM Tris, pH7.8, 1 mM EDTA | $^{16}$68.0 ± 12.0 | $^{16}$0.8 ± 0.2 | $^{16}$77.9 ± 6.2 |
| *C. albicans* FCA1 | 150 | 58% 86/148 | N/A | N/A | N/A | N/A | N/A |
| Ecoli CD | 427 | none | N/A | | $^{16}$11.7 ± 3.8 | $^{16}$17.9 + −4.4 | $^{16}$16.0 ± 0.8 |

EXAMPLE 4

Cytotoxicity Assay

The radiosensitizing effect of 5FC and 5FU in HT29, HT29/bCD, and HT29/yCD cells is determined using a standard clonogenic assay (3). Cells are treated with 5FC or 5FU at various concentrations for 24 h before irradiation at 37° C. in media containing 10% dialyzed serum. The radiation survival data are corrected for plating efficiency using a nonirradiated plate treated with 5FC or 5FU under the same conditions. The surviving fraction is plotted against the radiation dose, and curves fit using the linear-quadratic equation. The radiation sensitivity is expressed as the MID, which represents the area under the cell survival curve (1). Radiosensitization was expressed as the ER, which is defined as $MID_{control}/MID_{treated}$.

To determine the cytotoxic and radiosensitizing effect of 5FC and 5FU on bystander cells, cocultures of 90% bystander hygromycin-resistant HT29 cells and 10% puromycin-resistant CD-transduced HT29 cells are used. Cell survival of the hygromycin-resistant HT29 cells and puromycin-resistant CD-transduced HT29/cells is determined by plating the cells in selective media after treatment and assessed using a standard clonogenic assay as described above.

Cytotoxicity assay—transfected cells were seeded at a density of $1 \times 10^3$ cells/well in a 96-well microtiterplate containing 100 μl of culture medium. A set of sterile stock dilutions of the 10 mg/ml 5FC solution were prepared. One day later, increasing concentrations of 5FC was added to the wells, and a control well without the prodrug was included. After 5-7 days, the cells were washed with fresh medium and cytotoxicity was assessed by trypan blue exclusion, using a hemocytometer to quantify the results. The results are expected show increased cytotoxicity and bystander effect (up to 10 fold) per unit dose of 5FC compared with the bacteria, due to the increased conversion rate. Similarly, increased activity is expected in the CD-FUR1 fusion protein. It is not known how the C. kefyr protein will compare with the S. cerevisiae protein, but it is known that this protein has a 22-fold lower Km and a 4-fold higher Vmax for 5FC than bacterial CD protein. Thus, the activities are expected to be roughly equivalent or perhaps somewhat better in C. kefyr, once the assay is optimized for C. kefyr.

EXAMPLE 5

Antibodies

The peptidic fragments listed in the Table are synthesized and used to inject rabbits. Polyclonal antibodies are prepared therefrom and screened for activity. The best samples are chosen to prepare monoclonal antibodies.

TABLE 5

ANTIGENIC FRAGMENTS OF CD

| Residues from SEQ ID NO: 2 | Marker | Use |
| --- | --- | --- |
| 42-56 | Conserved residues | Broad-range autigenic fragments allow monitoring of CD from a variety of species. |
| 83-94 | | |
| 32-43 | C. kefyr specific | Specific antigenic fragments allow monitoring of C. keftr CD only. |
| 58-79 | | |
| 110-139 | | |
| 1-16 | | N-terminal detection (SEQ ID NO: 23) |
| M-136-152 | | C-terminal detection (SEQ ID NO: 24) |

To date, we have prepared a polyclonal antibody to the peptides from the amino and carboxyl terminals of the protein, according to standard techniques. The peptides were Met-Ala-Glu-Trp-Asp-Gln-Lys-Gly-Met-Asp-Lys-Ala-Tyr-Glu-Glu-Cys (SEQ ID NO: 23) and Cys-Lys-Glu-Phe-Ile-Glu-Lys-Arg-Pro-Glu-Asp-Trp-Tyr-Glu-Asp-Ile-Gly-Glu (SEQ ID NO: 24). Work is planned to isolate monoclonal antibodies for each.

EXAMPLE 6

Variants

The specific variants listed in table 2 are synthesized by site specific mutagenesis of SEQ ID NO: 1 or SEQ ID NO: 3. Additional variants may be made, however, it is suggested that the conserved residues indicated by the black boxes in FIG. 5 or 6 not be changed, unless one desires an inactive mutant. Further, changes within the cytidine and deoxycytidylate deaminase zinc-binding region (grey box) are also expected to be less well tolerated than changes outside this region. Residues that might be important to the C. kefyr CD are indicated in FIG. 6 as bold, These residues involve a change in charge as compared with the closest homolog and are in the binding region. Changes in these residues are expected to change function. Active variants are likely to be those that involve conservative changes in those residues not conserved in the 2 yeasts, particularly those outside the binding region.

Variants are expressed in E. coli and screened for activity using the assay described in example 3, or any suitable assay. Alternatively, random mutagenesis is performed and the products are similarly screened. In this manner, it will be possible to isolate variants with improved temperature stability at 37° C. and mutants with even better activity than that described herein.

Naturally occurring variants are isolated by screening populations of Candida kefyr with the cDNA of SEQ ID NO: 1 or 3 at high stringency. Alternatively, natural alleles can be isolated by ASO (allele specific oligonucleotide) screening using an array of overlapping oligonucleotides that provide complete coverage of SEQ ID NO: 1 or 3. In yet a third alternative, mutants with higher activity can be isolated by rescue screening yeast CD mutants grown on cytosine, as a source of pyrimidine.

EXAMPLE 7

CD-FUR1 Fusion

A fusion protein of the Candida kefyr CD gene and the uracil phosphoribosyltransferase genes (FUR1) is constructed as shown in SEQ ID NO: 10. A similar construct was made with the Saccharomyces cerevisiae CD (FCY1) (15). The FCY1-FUR1 fusion encoded a bifunctional chimeric protein that efficiently catalyzed the direct conversion of 5FC into the toxic metabolites 5FU and 5-FdUMP, thus bypassing the natural resistance of certain human tumor cells to 5FU. Unexpectedly, the cytosine deaminase activity of the fusion proteins was 100-fold higher than the wild type, resulting in greatly increased sensitivity to concentrations of 5FC (1000-fold increased sensitivity). Furthermore, the bystander effect was also more effective with the fusion protein than either FCY1or FUR1 alone or in combination. Because the Candida kefyr gene is 74% identical to the S. cerevisiae gene, it is expected to function similarly and experiments will be performed to confirm this.

Another type of multimodality therapy can be achieved with a replication-conditional herpes simplex virus 1 mutant, where the viral ribonucleotide reductase gene is disrupted by sequences encoding yeast cytosine deaminase. HSV1yCD-infected cells convert 5FC to 5FU without significantly reducing viral replication and oncolysis. HSV1yCD-infected cells are destroyed by viral replication, and uninfected cells are subjected to bystander killing from both progeny virion and extracellular diffusion of 5FU. This has been shown to increase anti-tumor effect. (18).

EXAMPLE 8

CD-Monoclonal Antibody Fusion

CD can be covalently attached to monoclonal antibodies, forming conjugates that bind to antigens on tumor cell surfaces and thus targeting the CD to a specific cell type. This experiment has been performed with the *S. cerevisiae* CD and the combination was specific for the antibody target (5). A similar effect can be achieved by expressing a CD-Monoclonal antibody fusion protein.

EXAMPLE 9

Suicide Gene Therapy

Preliminary suicide gene therapy in vivo results will be obtained using the nude mouse tumor model. The human colon cancer cell line HT29 will be grown in RPMI supplemented with 10% heat-inactivated calf serum, 2 mM glutamine, 100 IU/ml penicillin and 100 mg/ml streptomycin. Stable HT29 cell lines expressing either bacterial or various yeast CD genes (including the humanized *C. kefyr* CD gene) will be generated by viral infection using the retroviral vector LZR (Lazarus), or a gene-viral vector based on the adenovirus (19). Cells will be reseeded 24 h after infection to allow the formation of single colonies, which will be isolated and tested for CD activity. CD-positive clones will be used to generate mice tumor models.

Nude female mice (Nu/Nu CD-1, Charles River Laboratories, Wilmington, Mass.) of 7-8 weeks will receive injections (s.c.) in the flank with 5×10$^6$ viable HT29-CD cells, generated above. Tumors will be measured biweekly with calipers in 2 dimensions. Tumor volumes will calculated in mm$^3$ using the formula: (3.14/6) (L×W$^2$). When tumors are >50 mm$^3$ and measure an average volume of 100-150 mm$^3$, treatment will be started. Mice will receive injections daily (i.p.) with 500 mg/kg 5FC or 25 mg/kg 5FU 5 days a week for 2 weeks. Differences in the efficacy between treatments will be measured.

Suicide gene therapy has already been tested in several phase I and phase II clinical trials, and both safety and moderate efficacy have been shown. However, there is room for improvement of both transfection efficiencies and gene expression. It is anticipated that the use of a gene that codes for a more active 5FC to 5FU converting enzyme will provide benefit in suicide gene therapy, allowing the use of lower doses of 5FC. Clinical experiments with the new *C. kefyr* CD gene will not be undertaken for some time. In the interim, work is underway to optimize the reaction conditions for the *C. kefyr* CD protein, to confirm its cytotoxicity in cell toxicity assays, and in the nude mouse xenographic tumor model described above. It is anticipated that the *C. kefyr* CD gene will provide a benefit over the established bacterial gene, and may also prove to be an improvement over the *S. cerevisiae* gene.

EXAMPLE 11

Tumor Response Monitoring

The *C. kefyr* CD gene or its variants can be used to test an individual tumor cell's response to suicide gene therapy in vitro. Candidate tumor cells are transfected as above, and their responsiveness to the therapy assayed either in vitro or in the mouse tumor model. The tumor cells can be established tumor cell lines, or tumor cells biopsied from an individual. In this way, tumors most likely to benefit from suicide gene therapy using the CK gene can be identified.

CITES: All citations are hereby expressly incorporated by reference and are relisted here for convenience:
1. Fertil B, et al., *Radiat. Res.* (1984) 99: 83-93.
2. Di Vito M, et al., *Antimicrob. Agents Chemother.* (1986) 29(2):303-8.
3. Lawrence T S, *Cancer Res.* (1988) 48: 725-730.
4. Huber B E, et al., *Proc Natl Acad Sci USA*. (1991) 88:8039-8043.
5. Senter P D, et al., *Bioconjug. Chem.* (1991) 2(6):447-51.
6. Freeman S M, et al., *Cancer Res.* (1993) 53:5274-5283.
7. Higgins D G, et al., *Nucleic Acids Res*. (1994) 22:4673-80.
8. Sutton M A, et al., *J Urol*. (1996) 155:321.
9. Erbs P, et al., *Curr. Genet*. (1997) 31(1):1-6.
10. Hayden M S, et al., *Protein Expr. Purif.* (1998) 12(2):173-84.
11. WO9960008A1: CYTOSINE DEAMINASE GENE (from *S. cerevisiae*).
12. Blom N, et al., *J. Mol. Biol*. (1999) 294(5): 1351-1362.
13. Hamstra D A, et al., *Hum. Gene Ther*. (1999) 10(12): 1993-2003.
14. Tatusova T A & Madden T L, *FEMS Microbiol. Lett*. (1999) 174:274-250.
15. Erbs P, et al., *Cancer Res*. (2000) 60(14):3813-22.
16. Kievit E, et al., *Cancer Res*. 59, 1417-1421, Apr. 1, 1999
17. Martino R, et al., *Curr Drug Metab*. 2000 November; 1(3):271-303.
18. Nakamura H, et al., *Cancer Res*. 2001 Jul. 15; 61(14): 5447-52.
19. Qian Q, et al., Chin Med J (Engl) 2002 August; 115(8): 1213-1217; 13: Ganly I, et al., Clin Cancer Res. 2000 March; 6(3):798-806.

What is claimed is:

1. An isolated nucleic acid comprising a sequence that encodes the *C. kefyr* cytosine deaminase protein of SEQ ID NO: 2.

2. The nucleic acid of claim 1, wherein the nucleic acid is cDNA.

3. The nucleic acid of claim 2, wherein the nucleic acid comprises SEQ ID NO: 1.

4. The nucleic acid of claim 2, wherein the nucleic acid comprises SEQ ID NO: 7.

5. The nucleic acid of claim 2, wherein the nucleic acid comprises SEQ ID NO: 8.

6. The nucleic acid of claim 2, wherein the nucleic acid comprises SEQ ID NO: 9.

7. The nucleic acid of claim 2, wherein the nucleic acid comprises SEQ ID NO: 10.

8. The nucleic acid of claim 2, wherein the nucleic acid is optimized for expression in human cells.

9. The nucleic acid of claim 2, wherein the nucleic acid is optimized for expression in bacterial cells.

10. The nucleic acid of claim 2, wherein the nucleic acid is operably fused to a nucleic acid encoding a uracil phosphoribosyltransferase and a promoter.

11. A vector comprising the nucleic acid of any one of claims 1-10 operably linked to a promoter.

12. The vector of claim 11 wherein the operably linked promoter allows tissue specific expression in human tissue.

13. The vector of claim 11 wherein the operably linked promoter allows preferential expression in human cancer tissue.

14. An isolated nucleic acid that encodes a *C. kefyr* cytosine deaminase protein variant, wherein said variant is (i) a variant shown in Table 2 which is selected from the group consisting of I92L/L93I/I97L, T80S/T81S/T89S/Y95S, S42K/R47K, K129R/K136R, Δ1, Δ1-2, Δ1-8, Δ1-9, E3D, E38D, E114D, E138D, D33E, K11R, K69R, K124R, K129R, and K141R, or (ii) a 3'FLAG fusion protein of the variant of (i).

15. An isolated nucleic acid that encodes a *C. kefyr* cytosine deaminase protein, wherein (i) the protein comprises a sequence with at least 94% identity to SEQ ID NO: 2 over the entire length of SEQ ID NO: 2, and (ii) the protein converts 5-fluorocytosine to 5-fluorouracil.

16. A method of making *C. kefyr* cytosine deaminase protein, comprising growing a host cell comprising the vector of claim 11 in a nutrient medium and collecting the expressed *C. kefyr* cytosine deaminase protein.

17. The isolated nucleic acid of claim 15, wherein the nucleic acid comprises SEQ ID NO: 3.

* * * * *

SEQUENCE LISTING

```
<160> NUMBER OF SEQ ID NOS: 24

<210> SEQ ID NO 1
<211> LENGTH: 456
<212> TYPE: DNA
<213> ORGANISM: Candida kefyr

<400> SEQUENCE: 1
atggctgaat gggatcaaaa gggtatggac aaagcctatg aagaggctgc cattggatac      60
aaggagggag gtgtcccaat cggtggatgt ttaatcgata atttgaccgg tgagatttta     120
```

```
ggcagtggac acaacatgag attccaaaaa ggatcgccta ctttgcacgg tgagacttct      180
actttagaaa atgccggtag actaaagggg agtgtttaca agcattgtac tatgtacact      240
actttatctc catgtgatat gtgcacgggt gctattcttc tttatggaat tggccgtgtt      300
gtcattggcg aaaacgtcaa cttcaaaagc cctggagaag agtatctaac cagcagaggt      360
gtggaattga aggttgtaga tgacaaacgc tgtatcgata taatgaagga gttcattgaa      420
aagagaccag aagactggta cgaagacatt ggcgaa                                456

<210> SEQ ID NO 2
<211> LENGTH: 152
<212> TYPE: PRT
<213> ORGANISM: Candida kefyr

<400> SEQUENCE: 2

Met Ala Glu Trp Asp Gln Lys Gly Met Asp Lys Ala Tyr Glu Glu Ala
1               5                   10                  15

Ala Ile Gly Tyr Lys Glu Gly Gly Val Pro Ile Gly Gly Cys Leu Ile
                20                  25                  30

Asp Asn Leu Thr Gly Glu Ile Leu Gly Ser Gly His Asn Met Arg Phe
            35                  40                  45

Gln Lys Gly Ser Pro Thr Leu His Gly Glu Thr Ser Thr Leu Glu Asn
        50                  55                  60

Ala Gly Arg Leu Lys Gly Ser Val Tyr Lys His Cys Thr Met Tyr Thr
65                  70                  75                  80

Thr Leu Ser Pro Cys Asp Met Cys Thr Gly Ala Ile Leu Leu Tyr Gly
                85                  90                  95

Ile Gly Arg Val Val Ile Gly Glu Asn Val Asn Phe Lys Ser Pro Gly
                100                 105                 110

Glu Glu Tyr Leu Thr Ser Arg Gly Val Glu Leu Lys Val Val Asp Asp
            115                 120                 125

Lys Arg Cys Ile Asp Ile Met Lys Glu Phe Ile Glu Lys Arg Pro Glu
        130                 135                 140

Asp Trp Tyr Glu Asp Ile Gly Glu
145                 150

<210> SEQ ID NO 3
<211> LENGTH: 456
<212> TYPE: DNA
<213> ORGANISM: Candida kefyr

<400> SEQUENCE: 3
atggctgaat gggatcaaaa gggtatggac aaagcctatg aagaggctgc cattggatac      60
aaggagggag gtgttccaat cggtggatgt ttaatcgaca atttgaccgg tgagatttta      120
ggcagtggac acaacatgag attccaaaaa ggatcgccaa ctttgcacgg tgagacttct      180
actttagaaa atgccggtag actaaagggg agtgtttaca agcattgtac tatgtacact      240 acctatctc catgtgatat gtgcacgggt gctattcttc tttatggaat tggccgtgtt      300
gtcattggtg aaaacgtcaa cttcaaaagc cctggggaag agtatctaac cagcagaggt      360
gtggagttga aggttgtaga tgacaaacgc tgtatcgata taatgaagga gttcattgaa      420
aagagaccag aagactggta cgaagacatt ggcgaa                                456

<210> SEQ ID NO 4
<211> LENGTH: 152
<212> TYPE: PRT
```

-continued

<213> ORGANISM: Candida kefyr

<400> SEQUENCE: 4

```
Met Ala Glu Trp Asp Gln Lys Gly Met Asp Lys Ala Tyr Glu Ala
1               5                   10                  15

Ala Ile Gly Tyr Lys Glu Gly Val Pro Ile Gly Gly Cys Leu Ile
                20                  25                  30

Glu Asn Leu Thr Gly Glu Ile Leu Gly Ser Gly His Asn Met Arg Phe
            35                  40                  45

Gln Lys Gly Ser Pro Thr Leu His Gly Glu Thr Ser Thr Leu Glu Asn
        50                  55                      60

Ala Gly Arg Leu Lys Gly Ser Val Tyr Lys His Cys Thr Met Tyr Thr
65                  70                  75                  80

Thr Leu Ser Pro Cys Asp Met Cys Thr Gly Ala Ile Leu Leu Tyr Gly
                85                  90                  95

Ile Gly Arg Val Val Ile Gly Glu Asn Val Asn Phe Lys Ser Pro Gly
                100                 105                 110

Glu Glu Tyr Leu Thr Ser Arg Gly Val Glu Leu Lys Val Val Asp Asp
            115                 120                 125

Lys Arg Cys Ile Asp Ile Met Lys Glu Phe Ile Glu Lys Arg Pro Glu
        130                 135                     140

Asp Trp Tyr Glu Asp Ile Gly Glu
145                 150
```

<210> SEQ ID NO 5
<211> LENGTH: 158
<212> TYPE: PRT
<213> ORGANISM: Saccharomyces cerevisiae
<300> PUBLICATION INFORMATION:
<301> AUTHORS: Goffeau A, Barrell BG, Bussey H, Davis RW, Dujon B,
      Feldmann H, Galibert F, Hoheisel JD, Jacq C, Johnston M, Louis
      EJ, Mewes HW, Murakami Y, Philippsen P, Tettelin H, Oliver SG.
<302> TITLE: Life with 6000 genes.
<303> JOURNAL: Science
<304> VOLUME: 274
<305> ISSUE: 5287
<306> PAGES: 546, 563-7
<307> DATE: 1996-10-25
<308> DATABASE ACCESSION NUMBER: GENBANK / NC_001148
<309> DATABASE ENTRY DATE: 1999-09-11
<313> RELEVANT RESIDUES: (1)..(158)
<300> PUBLICATION INFORMATION:
<301> AUTHORS: Erbs,P., Exinger,F. and Jund,R.
<302> TITLE: Characterization of the Saccharomyces cerevisiae FCY1 gene
      encodingcytosine deaminase and its homologue FCA1 of Candida
      albicans
<303> JOURNAL: Current Genetics
<304> VOLUME: 31
<305> ISSUE: 1
<306> PAGES: 1-6
<307> DATE: 1997-01-01
<308> DATABASE ACCESSION NUMBER: GENBANK / AAC13409
<309> DATABASE ENTRY DATE: 1996-04-16
<313> RELEVANT RESIDUES: (1)..(158)
<300> PUBLICATION INFORMATION:
<308> DATABASE ACCESSION NUMBER: GENBANK / NP_015387
<309> DATABASE ENTRY DATE: 1999-09-11
<313> RELEVANT RESIDUES: (1)..(158)

<400> SEQUENCE: 5

```
Met Val Thr Gly Gly Met Ala Ser Lys Trp Asp Gln Lys Gly Met Asp
1               5                   10                  15

Ile Ala Tyr Glu Glu Ala Ala Leu Gly Tyr Lys Glu Gly Gly Val Pro
                20                  25                  30

Ile Gly Gly Cys Leu Ile Asn Asn Lys Asp Gly Ser Val Leu Gly Arg
```

35                  40                  45
Gly His Asn Met Arg Phe Gln Lys Gly Ser Ala Thr Leu His Gly Glu
         50                  55                  60

Ile Ser Thr Leu Glu Asn Cys Gly Arg Leu Glu Gly Lys Val Tyr Lys
 65                  70                  75                  80

Asp Thr Thr Leu Tyr Thr Thr Leu Ser Pro Cys Asp Met Cys Thr Gly
                     85                  90                  95

Ala Ile Ile Met Tyr Gly Ile Pro Arg Cys Val Val Gly Glu Asn Val
                100                 105                 110

Asn Phe Lys Ser Lys Gly Glu Lys Tyr Leu Gln Thr Arg Gly His Glu
            115                 120                 125

Val Val Val Asp Asp Glu Arg Cys Lys Lys Ile Met Lys Gln Phe
    130                 135                 140

Ile Asp Glu Arg Pro Gln Asp Trp Phe Glu Ile Gly Glu
145                 150                 155

<210> SEQ ID NO 6
<211> LENGTH: 150
<212> TYPE: PRT
<213> ORGANISM: Candida albicans
<300> PUBLICATION INFORMATION:
<301> AUTHORS: Erbs,P., Exinger,F. and Jund,R.
<302> TITLE: Characterization of the Saccharomyces cerevisiae FCY1 gene
       encoding cytosine deaminase and its homologue FCA1 of Candida
       albicans
<303> JOURNAL: Current Genetics
<304> VOLUME: 31
<305> ISSUE: 1
<306> PAGES: 1-6
<307> DATE: 1997-01-01
<308> DATABASE ACCESSION NUMBER: GENBANK / P78594
<309> DATABASE ENTRY DATE: 1997-11-01
<313> RELEVANT RESIDUES: (1)..(150)
<300> PUBLICATION INFORMATION:
<308> DATABASE ACCESSION NUMBER: GENBANK / P78594
<309> DATABASE ENTRY DATE: 1997-11-01
<313> RELEVANT RESIDUES: (1)..(150)

<400> SEQUENCE: 6

Met Thr Phe Asp Asp Lys Lys Gly Leu Gln Val Ala Leu Asp Gln Ala
 1               5                  10                  15

Lys Lys Ser Tyr Ser Glu Gly Gly Ile Pro Ile Gly Ser Cys Ile Ile
                20                  25                  30

Ser Ser Asp Asp Thr Val Leu Gly Gln Gly His Asn Glu Arg Ile Gln
            35                  40                  45

Lys His Ser Ala Ile Leu His Gly Glu Met Ser Ala Leu Glu Asn Ala
 50                  55                  60

Gly Arg Leu Pro Gly Lys Thr Tyr Lys Asp Cys Thr Ile Tyr Thr Thr
 65                  70                  75                  80

Leu Ser Pro Cys Ser Met Cys Thr Gly Ala Ile Leu Leu Tyr Gly Phe
                     85                  90                  95

Lys Arg Val Val Met Gly Glu Asn Val Asn Phe Leu Gly Asn Glu Lys
                100                 105                 110

Leu Leu Ile Glu Asn Gly Val Glu Val Val Asn Leu Asn Asp Gln Glu
            115                 120                 125

Cys Ile Asp Leu Met Ala Lys Phe Ile Lys Lys Pro Gln Asp Trp
    130                 135                 140

Asn Glu Asp Ile Gly Glu
145             150

<210> SEQ ID NO 7
<211> LENGTH: 459
<212> TYPE: DNA
<213> ORGANISM: Candida kefyr

<400> SEQUENCE: 7

| | | | | | |
|---|---|---|---|---|---|
| atggcggaat | gggatcagaa | aggcatggat | aaagcgtatg | aagaagcggc | gattggctat | 60 |
| aaagaaggcg | gcgtgccgat | tggcggctgc | ctgattgata | acctgaccgg | cgaaattctg | 120 |
| ggcagcggcc | ataacatgcg | ctttcagaaa | ggcagcccga | ccctgcatgg | cgaaaccagc | 180 |
| accctggaaa | acgcgggccg | cctgaaaggc | agcgtgtata | acattgcac | catgtatacc | 240 |
| accctgagcc | cgtgcgatat | gtgcaccggc | gcgattctgc | tgtatggcat | tggccgcgtg | 300 |
| gtgattggcg | aaaacgtgaa | ctttaaaagc | ccgggcgaag | aatatctgac | cagccgcggc | 360 |
| gtggaactga | agtggtgga | tgataaacgc | tgcattgata | ttatgaaaga | atttattgaa | 420 |
| aaacgcccgg | aagattggta | tgaagatatt | ggcgaataa | | | 459 |

<210> SEQ ID NO 8
<211> LENGTH: 459
<212> TYPE: DNA
<213> ORGANISM: Candida kefyr

<400> SEQUENCE: 8

| | | | | | |
|---|---|---|---|---|---|
| atggccgagt | gggaccagaa | gggcatggac | aaggcctacg | aggaggccgc | catcggctac | 60 |
| aaggagggcg | gcgtgcccat | cggcggctgc | ctgatcgaca | acctgaccgg | cgagatcctg | 120 |
| ggcagcggcc | acaacatgag | attccagaag | ggcagcccca | ccctgcacgg | cgagaccagc | 180 |
| accctggaga | acgccggcag | actgaagggc | agcgtgtaca | agcactgcac | catgtacacc | 240 |
| accctgagcc | cctgcgacat | gtgcaccggc | gccatcctgc | tgtacggcat | cggcagagtg | 300 |
| gtgatcggcg | agaacgtgaa | cttcaagagc | cccggcgagg | agtacctgac | cagcagaggc | 360 |
| gtggagctga | agtggtgga | cgacaagaga | tgcatcgaca | tcatgaagga | gttcatcgag | 420 |
| aagagacccg | aggactggta | cgaggacatc | ggcgagtga | | | 459 |

<210> SEQ ID NO 9
<211> LENGTH: 459
<212> TYPE: DNA
<213> ORGANISM: Candida kefyr

<400> SEQUENCE: 9

| | | | | | |
|---|---|---|---|---|---|
| atggctgagt | gggaccagaa | gggcatggac | aaggcctatg | aggaggctgc | tatcgggtac | 60 |
| aaggaggggg | gggtccccat | tgggggtgt | ctgattgaca | acctgacagg | ggagatcctg | 120 |
| gggagtggcc | acaacatgag | attccagaag | gggtccccca | ccctccatgg | ggagaccctcc | 180 |
| accctggaga | atgctgggag | actgaagggg | tctgtgtaca | acactgtac | catgtacacc | 240 |
| accctgtccc | cctgtgacat | gtgtacaggg | gccatcctcc | tgtatgggat | gggagagtg | 300 |
| gtgatcgggg | agaatgtgaa | cttcaagtcc | cctggggagg | agtacctgac | ctccagaggg | 360 |
| gtggaactga | agtggtgga | tgacaagaga | tgtatcgaca | tcatgaagga | gttcattgag | 420 |
| aagagacctg | aggactggta | tgaggacatt | ggggagtga | | | 459 |

<210> SEQ ID NO 10
<211> LENGTH: 1104
<212> TYPE: DNA
<213> ORGANISM: Candida kefyr

<400> SEQUENCE: 10

-continued

```
atggctgagt gggaccagaa gggaatggac aaggcctatg aggaggctgc cattggatac      60
aaggagggag gagtccctat tggaggatgt ctgattgaca acctgacagg agagatcctg     120
ggatctggac acaacatgag attccagaag ggatccccta ccctccatgg agagacctcc     180
accctggaga atgctggaag actgaaggga tctgtgtaca acactgtac catgtacacc     240 accctgtccc cttgtgacat gtgtacagga gccatcctcc tgtatggaat tggaagagtg    300
gtgattggag agaatgtgaa cttcaagtcc cctggagagg agtacctgac ctccagagga   360
gtggaactga aggtggtgga tgacaagaga tgtattgaca tcatgaagga gttcattgag    420
aagagacctg aggactggta tgaggacatt ggagaggcct ctgaaccttt caagaatgtg    480
tacctcctcc ctcagaccaa ccaactactg ggactgtaca ccatcatcag aaacaagaac    540
accaccagac ctgacttcat cttctactct gacagaatca tcagactcct ggtggaggag    600
ggactgaacc acctccctgt ccagaaacag attgtggaga cagacaccaa tgagaacttt    660
gagggagtgt ccttcatggg aaagatctgt ggagtgtcca ttgtgagagc tggagagtcc    720
atggaacagg gactgagaga ctgttgtaga tctgtgagaa ttggaaagat cctgatccag    780
agagatgagg agacagccct ccctaaactg ttctatgaga aactccctga ggacatctct    840
gagagatatg tgttcctcct ggaccctatg ctggccacag gaggatctgc catcatggcc    900
acagaggtcc tgatcaagag aggagtgaaa cctgagagaa tctacttcct gaacctgatc    960
tgttccaagg agggaattga gaagtaccat gctgccttcc ctgaggtgag aattgtgaca   1020
ggagccctgg acagaggact ggatgagaac aagtacctgg tccctggact gggagacttt   1080
ggagacagat actactgtgt gtga                                            1104
```

```
<210> SEQ ID NO 11
<211> LENGTH: 18
<212> TYPE: DNA
<213> ORGANISM: Unknown
<220> FEATURE:
<223> OTHER INFORMATION: FRAGMENT

<400> SEQUENCE: 11
atgtgtactg gtgctatt                                                    18

<210> SEQ ID NO 12
<211> LENGTH: 18
<212> TYPE: DNA
<213> ORGANISM: Unknown
<220> FEATURE:
<223> OTHER INFORMATION: Fragment

<400> SEQUENCE: 12
ggtgaaaacg ttaacttc                                                    18

<210> SEQ ID NO 13
<211> LENGTH: 18
<212> TYPE: DNA
<213> ORGANISM: Unknown
<220> FEATURE:
<223> OTHER INFORMATION: Fragment

<400> SEQUENCE: 13
ggtgaaaacg tcaacttc                                                    18

<210> SEQ ID NO 14
<211> LENGTH: 15
<212> TYPE: DNA
<213> ORGANISM: Unknown
```

```
<220> FEATURE:
<223> OTHER INFORMATION: Fragment

<400> SEQUENCE: 14
gaagatattg gtgaa                                                         15

<210> SEQ ID NO 15
<211> LENGTH: 15
<212> TYPE: DNA
<213> ORGANISM: Unknown
<220> FEATURE:
<223> OTHER INFORMATION: Fragment

<400> SEQUENCE: 15
gaagacattg gtgaa                                                         15

<210> SEQ ID NO 16
<211> LENGTH: 30
<212> TYPE: DNA
<213> ORGANISM: Unknown
<220> FEATURE:
<223> OTHER INFORMATION: Fragment

<400> SEQUENCE: 16
ggccgtgttg tcattggtga aaacgtcaac                                         30

<210> SEQ ID NO 17
<211> LENGTH: 30
<212> TYPE: DNA
<213> ORGANISM: Unknown
<220> FEATURE:
<223> OTHER INFORMATION: Fragment

<400> SEQUENCE: 17
ggtctctttt caatgaactc cttcattata                                         30

<210> SEQ ID NO 18
<211> LENGTH: 33
<212> TYPE: DNA
<213> ORGANISM: Unknown
<220> FEATURE:
<223> OTHER INFORMATION: Fragment

<400> SEQUENCE: 18
gttgtcattg gtgaaaacgt caacttcaaa agc                                     33

<210> SEQ ID NO 19
<211> LENGTH: 30
<212> TYPE: DNA
<213> ORGANISM: Unknown
<220> FEATURE:
<223> OTHER INFORMATION: Fragment

<400> SEQUENCE: 19
aatgaactcc ttcattatat cgatacagcg                                         30

<210> SEQ ID NO 20
<211> LENGTH: 39
<212> TYPE: DNA
<213> ORGANISM: Unknown
<220> FEATURE:
<223> OTHER INFORMATION: FRAGMENT

<400> SEQUENCE: 20
cttgggatcc gccaccatgg ctgaatggga tcaaaaggg                               39
```

```
<210> SEQ ID NO 21
<211> LENGTH: 32
<212> TYPE: DNA
<213> ORGANISM: Unknown
<220> FEATURE:
<223> OTHER INFORMATION: Fragment

<400> SEQUENCE: 21
cttgctcgag ttcgccaatg tcttcgtacc ag                                   32

<210> SEQ ID NO 22
<211> LENGTH: 33
<212> TYPE: DNA
<213> ORGANISM: Unknown
<220> FEATURE:
<223> OTHER INFORMATION: Fragment

<400> SEQUENCE: 22
cttgctgcag ctattcgcca atgtcttcgt acc                                  33

<210> SEQ ID NO 23
<211> LENGTH: 16
<212> TYPE: PRT
<213> ORGANISM: Unknown
<220> FEATURE:
<223> OTHER INFORMATION: Fragment

<400> SEQUENCE: 23

Met Ala Glu Trp Asp Gln Lys Gly Met Asp Lys Ala Tyr Glu Glu Cys
1               5                   10                  15

<210> SEQ ID NO 24
<211> LENGTH: 18
<212> TYPE: PRT
<213> ORGANISM: Unknown
<220> FEATURE:
<223> OTHER INFORMATION: Fragment

<400> SEQUENCE: 24

Cys Lys Glu Phe Ile Glu Lys Arg Pro Glu Asp Trp Tyr Glu Asp Ile
1               5                   10                  15

Gly Glu
```